United States Patent
White, Jr. et al.

(10) Patent No.: US 6,713,049 B1
(45) Date of Patent: Mar. 30, 2004

(54) ORAL COMPOSITIONS PROVIDING OPTIMAL SURFACE CONDITIONING

(75) Inventors: Donald J. White, Jr., Fairfield, OH (US); William M. Glandorf, Mason, OH (US); Henk J. Busscher, Thesinge (NL); Jeannine R. Knight, Beavercreek, OH (US); Arif A. Baig, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 398 days.

(21) Appl. No.: 09/710,250

(22) Filed: Nov. 10, 2000

Related U.S. Application Data

(60) Provisional application No. 60/165,351, filed on Nov. 12, 1999.

(51) Int. Cl.⁷ .................................................. A61K 7/16
(52) U.S. Cl. ........................................ 424/57; 424/49
(58) Field of Search .......................... 424/49–88, 57

(56) References Cited

U.S. PATENT DOCUMENTS

| | | | |
|---|---|---|---|
| 2,191,199 A | | 2/1940 | Hall ............................ 167/93 |
| 2,409,718 A | | 10/1946 | Snell et al. ................ 252/106 |
| 2,498,344 A | | 2/1950 | Rider et al. ............... 252/103 |
| 2,876,167 A | * | 3/1959 | Manahan .................... 167/93 |
| 2,946,725 A | * | 7/1960 | Norris et al. ............... 167/93 |
| 3,004,897 A | * | 10/1961 | Shore ......................... 167/93 |
| 3,105,798 A | * | 10/1963 | Holliday et al. ............. 167/93 |
| 3,130,002 A | | 4/1964 | Fuchs et al. .................. 21/2.7 |
| 3,227,618 A | * | 1/1966 | Manahan .................... 167/93 |
| 3,562,385 A | | 2/1971 | Block et al. ................ 424/54 |
| 3,634,585 A | * | 1/1972 | Manahan .................... 424/52 |
| 3,862,307 A | | 1/1975 | DiGiulio ..................... 424/52 |
| 3,932,603 A | | 1/1976 | Haas ........................... 424/49 |
| 3,934,002 A | * | 1/1976 | Haefele ....................... 424/54 |
| 3,959,458 A | | 5/1976 | Agricola et al. ............. 424/52 |
| 4,051,234 A | | 9/1977 | Gieske et al. ............... 424/52 |
| 4,206,215 A | | 6/1980 | Bailey ....................... 424/263 |
| 4,244,931 A | | 1/1981 | Jarvis et al. ............... 423/266 |
| 4,247,526 A | | 1/1981 | Jarvis et al. ............... 423/266 |
| 4,340,583 A | | 7/1982 | Wason ........................ 424/52 |
| 4,357,318 A | | 11/1982 | Shah et al. .................. 424/57 |
| 4,370,314 A | | 1/1983 | Gaffar ........................ 424/54 |
| 4,452,713 A | | 6/1984 | Small ......................... 252/99 |
| 4,459,281 A | | 7/1984 | Sipos ......................... 424/52 |
| 4,460,565 A | * | 7/1984 | Westrate ..................... 424/52 |
| 4,515,772 A | | 5/1985 | Parran, Jr. et al. ......... 424/57 |
| 4,528,180 A | | 7/1985 | Schaeffer ................... 424/52 |
| 4,528,181 A | | 7/1985 | Morton et al. ............. 424/52 |
| 4,562,066 A | | 12/1985 | Hayes et al. ............... 424/52 |
| 4,568,540 A | | 2/1986 | Asano et al. ............... 424/52 |
| 4,627,977 A | * | 12/1986 | Gaffar et al. ............... 424/52 |
| 4,664,906 A | | 5/1987 | Sipos ......................... 424/49 |
| 4,687,663 A | | 8/1987 | Schaeffer ................... 424/52 |
| 4,842,847 A | * | 6/1989 | Amjad ........................ 424/52 |
| 4,849,213 A | | 7/1989 | Schaeffer ................... 424/53 |
| 4,892,725 A | * | 1/1990 | Amjad ........................ 424/52 |
| 4,894,220 A | | 1/1990 | Nabi et al. .................. 424/52 |
| 4,913,895 A | * | 4/1990 | Miyake et al. ............. 424/52 |
| 4,939,284 A | | 7/1990 | Degenhardt ............... 558/142 |
| 4,980,152 A | | 12/1990 | Frazier et al. .............. 424/52 |
| 5,000,944 A | | 3/1991 | Prencipe et al. ........... 424/57 |
| 5,004,597 A | * | 4/1991 | Majeti ........................ 424/52 |
| 5,009,882 A | | 4/1991 | Degenhardt et al. ....... 424/52 |
| 5,011,913 A | | 4/1991 | Benedict et al. ......... 530/390 |
| 5,015,466 A | | 5/1991 | Parran, Jr. et al. ......... 424/52 |
| 5,017,363 A | | 5/1991 | Suhonen ..................... 424/52 |
| 5,041,280 A | | 8/1991 | Smigel ....................... 424/52 |

(List continued on next page.)

FOREIGN PATENT DOCUMENTS

| | | | |
|---|---|---|---|
| BE | 837701 | 7/1976 | |
| CA | 570803 | 2/1959 | |
| EP | 0026539 | 9/1980 | ............ A61K/7/16 |
| GB | 490384 | 8/1938 | |
| WO | WO94/14406 | 7/1974 | ............ A61K/7/16 |
| WO | WO94/14407 | 7/1994 | ............ A61K/7/16 |
| WO | WO95/09603 | 4/1995 | ............ A61K/7/20 |

(List continued on next page.)

OTHER PUBLICATIONS

Draus, F.J., et al., "Pyrophosphate and Hexametaphosphate Effects in In Vitro Calculus Formation", Archs Oral Biol., vol. 15, pp. 893–896 (1970).

Opinion, Ex Parte Novitski, U.S. Patent and Trademark, Board of Patent Appeals and Interferences, Decided Jan. 22, 1993, No. 92–1680, USPQ2d 1389.

Kerr, D.A., et al., "Sodium Hexametaphosphate as an Aid in the Treatment of Periodontal Disease", Journal of Dentistry, 23:313–316 (1944).

U.S. patent application Ser. No. 09/710,209, Glandorf et al., filed Nov. 10, 2000.

U.S. patent application Ser. No. 09/710,440, Glandorf et al., filed Nov. 10, 2000.

*Primary Examiner*—Shep K. Rose

(57) ABSTRACT

The present invention relates to oral composition comprising a polymeric surface active agent wherein the oral composition provides surface conditioning effects on a subject's teeth and/or oral mucosa. The surface conditioning effects include (a) increased hydrophilic character of oral surfaces as measured by a decrease in water contact angles or an increase in anionic surface charge and surface charge density and (b) decreased pellicle film thickness. The present invention also relates to methods of providing surface conditioning effects to a subject's tooth and mucosal surfaces and methods of preventing and controlling tartar and tooth staining by administering to the subject an oral composition comprising a polymeric surface active agent.

1 Claim, No Drawings

U.S. PATENT DOCUMENTS

| | | | |
|---|---|---|---|
| 5,093,170 A | 3/1992 | Degenhardt et al. | 425/55 |
| 5,094,844 A | 3/1992 | Gaffar et al. | 424/52 |
| 5,096,701 A | 3/1992 | White, Jr. et al. | 424/52 |
| 5,098,711 A | 3/1992 | Hill et al. | 424/401 |
| 5,145,666 A | 9/1992 | Lukacovic et al. | 424/52 |
| 5,176,900 A | 1/1993 | White, Jr. et al. | 424/52 |
| 5,192,532 A | 3/1993 | Guay et al. | 424/53 |
| 5,213,789 A | 5/1993 | Degenhardt et al. | 424/52 |
| 5,213,790 A | 5/1993 | Lukacovic et al. | 424/52 |
| 5,256,402 A | 10/1993 | Prencipe et al. | 424/53 |
| 5,281,410 A | 1/1994 | Lukacovic et al. | 424/52 |
| 5,281,411 A * | 1/1994 | Majeti et al. | 424/52 |
| 5,292,501 A | 3/1994 | Degenhardt et al. | 424/49 |
| 5,296,215 A | 3/1994 | Burke et al. | 424/49 |
| 5,296,217 A | 3/1994 | Stookey | 424/57 |
| 5,320,831 A | 6/1994 | Majeti et al. | 424/52 |
| 5,320,832 A | 6/1994 | Catiis et al. | 424/52 |
| 5,338,537 A | 8/1994 | White, Jr. et al. | 424/57 |
| 5,368,844 A | 11/1994 | Gaffar et al. | 424/49 |
| 5,372,802 A | 12/1994 | Barrows et al. | 424/52 |
| 5,496,540 A | 3/1996 | Gaffar et al. | 424/49 |
| 5,565,190 A | 10/1996 | Santalucia et al. | 424/53 |
| 5,571,501 A | 11/1996 | Toy | 424/49 |
| 5,578,293 A * | 11/1996 | Prencipe et al. | 424/52 |
| 5,589,160 A | 12/1996 | Rice | 424/49 |
| 5,599,525 A | 2/1997 | Hsu et al. | 424/49 |
| 5,601,803 A | 2/1997 | Masters et al. | 474/49 |
| 5,603,920 A | 2/1997 | Rice | 424/49 |
| 5,614,174 A | 3/1997 | Hsu et al. | 424/49 |
| 5,616,313 A | 4/1997 | Williams et al. | 424/49 |
| 5,630,999 A | 5/1997 | Burke et al. | 424/49 |
| 5,632,972 A | 5/1997 | Williams et al. | 424/49 |
| 5,648,064 A | 7/1997 | Gaffar et al. | 424/53 |
| 5,651,958 A | 7/1997 | Rice | 424/49 |
| 5,658,553 A | 8/1997 | Rice | 424/49 |
| 5,716,600 A * | 2/1998 | Zahradnik et al. | 424/52 |
| 5,716,601 A | 2/1998 | Rice | 424/52 |
| 5,780,015 A | 7/1998 | Fisher et al. | 424/52 |
| 5,814,303 A | 9/1998 | Williams et al. | 424/57 |
| 5,820,854 A | 10/1998 | Glandorf | 424/52 |
| 5,833,952 A | 11/1998 | Grigor et al. | 424/49 |
| 5,885,553 A | 3/1999 | Michael | 424/49 |
| 5,885,554 A | 3/1999 | Michael et al. | 424/49 |
| 5,891,448 A | 4/1999 | Chow et al. | 424/400 |
| 5,902,568 A | 5/1999 | Ryles et al. | 424/53 |
| 5,939,052 A * | 8/1999 | White et al. | 424/52 |
| 5,948,390 A | 9/1999 | Nelson et al. | 424/54 |
| 5,980,776 A | 11/1999 | Zakikhani et al. | 252/175 |
| 6,187,295 B1 * | 2/2001 | Glandorf | 424/52 |
| 6,350,436 B1 * | 2/2002 | Glandorf et al. | 424/52 |

FOREIGN PATENT DOCUMENTS

| | | | |
|---|---|---|---|
| WO | WO97/46462 | 12/1997 | B65D/35/22 |
| WO | WO98/04234 | 2/1998 | A61K/7/16 |
| WO | WO98/51271 | 4/1998 | A61K/7/26 |
| WO | WO98/47475 | 10/1998 | A61K/7/16 |
| WO | WO99/20238 | 4/1999 | A61K/7/16 |
| WO | WO99/53893 | 10/1999 | A61K/7/16 |

* cited by examiner

US 6,713,049 B1

ORAL COMPOSITIONS PROVIDING OPTIMAL SURFACE CONDITIONING

CROSS-REFERENCE TO RELATED APPLICATIONS

This application claims the benefit of U.S. Provisional Application No. 60/165,351, filed Nov. 12, 1999.

TECHNICAL FIELD

The present invention relates to oral care compositions containing polymeric surface active agents, including polyphosphates, which provide novel surface conditioning reactions to oral surfaces such as the teeth and mucosa. This leads to improved cleaning impression delivered by these oral care products.

BACKGROUND OF THE INVENTION

Oral care products such as toothpastes are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral products include the control of plaque and calculus formation, removal and prevention of tooth stain, tooth whitening, breath freshening, and overall improvements in mouth feel impression which can be broadly characterized as mouth feel aesthetics.

In general, virtually all disclosures related to oral care products include some mention of the addition of flavoring components, humectants or other ingredients designed to increase aesthetic desirability of compositions. In some cases, specialized ingredients are added to specifically mask negative characteristics of other ingredients. For example, U.S. Pat. No. 5,945,088 to DelliSanti et al., U.S. Pat. No. 4,945,087 to Talwar et al., and U.S. Pat. No. 4,853,247 to Barcelon et al. describe the addition of certain ingredients to oral care products to mask negative characteristics of essential oils or phenolic compounds. Most ingredients are added with focus on the flavoring characteristics in masking the formula base.

While the prior art has addressed some of the formulation issues of oral care products relating to aesthetic desirability, there continues to be a need in the area, particularly in improving mouth feel aesthetics provided by oral care products.

U.S. Pat. No. 5,939,052 to White Jr., et al. describes stable oral formulations containing linear condensed polyphosphate polymers and ionic fluoride. These ingredients are prepared in physically separated packaging compartments to ensure adequate composition stability. Detailed studies of the therapeutic and cosmetic benefits of these formulations have revealed surprising levels of fluoride anticaries efficacy, along with improved efficacy in calculus prevention.

Research has now revealed new and surprising additional benefits of oral compositions containing certain surface-active polymers including the polyphosphates described in U.S. Pat. No. 5,939,052. The present invention relates to providing these new benefits, which are related to effects on the surface chemical characteristics of mucosal and tooth surfaces and which in turn, provide remarkable cleaning impression and positive mouth feel characteristics for extended periods of time following use of the present compositions.

SUMMARY OF THE INVENTION

The present invention is directed to oral composition comprising a polymeric surface active agent wherein the oral composition provides surface conditioning effects on a subject's teeth and/or oral mucosa. The surface conditioning effects include consumer perceived improvements in clean mouth and clean and smooth teeth impression. In vivo and in vitro studies show that treatment of oral surfaces with oral products containing appropriate surface conditioning polymers results in decreased oral surface water contact angles associated with the provision of increased hydrophilic character to oral surfaces. In vivo studies show a direct correlation with consumer desirable clean teeth and smooth teeth perception within the range of surface effects provided by these agents. In vitro studies support that the surface energy changes are complemented by decreases in the quantity of pellicle film at these surfaces as well as changes in the surface charge and charge density. The present invention also relates to methods of providing surface conditioning effects to a subject's teeth and mucosal surfaces and of controlling tartar and preventing tooth staining comprising administering to the subject an oral composition comprising a polymeric surface active agent.

These and other features, aspects, and advantages of the present invention will become evident to those skilled in the art from the detailed description which follows.

DETAILED DESCRIPTION OF THE INVENTION

While the specification concludes with claims which particularly point out and distinctly claim the invention, it is believed the present invention will be better understood from the following description.

All percentages and ratios used herein are by weight of the specific dentifrice composition and not of the overall oral formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

The oral composition of the present invention may be in the form of a toothpaste, dentifrice, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side.

The term "dispenser", as used herein, means any pump, tube, or container suitable for dispensing toothpaste.

The oral composition may be a single phase oral composition or may be a combination of two or more oral compositions. The oral composition is a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include fluoride ion sources, additional anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque biofilms.

The present invention is directed to oral compositions containing polymeric surface active agents which provide improved intraoral cleaning impression and smooth tooth surface impression derived from the surface conditioning effects of the polymeric surface active agents. In particular, the polymeric surface active agents provide chemical control of tooth and mucosal surface energy characteristics including modification of surface hydrophilic and hydrophobic properties.

The present compositions comprise essential components, as well as optional components. The essential and optional components of the compositions of the present invention are described in the following paragraphs.

Polymeric Surface Active Agent

The present invention includes a polymeric surface active agent as an essential ingredient. The polymeric surface active agents will provide the surface conditioning effects which produce desirable effects on surface thermodynamic properties and surface film properties, which impart improved clean feel aesthetics both during and most importantly, following tooth brushing. Many of these polymeric agents are also known or expected to provide tartar control or antistain/whitening activities when applied in oral compositions, hence providing dual clinical actions in improving the appearance of teeth and their tactile impression to consumers.

The polymeric surface active agents include any agent which will produce the desired surface conditioning effects. The desired surface conditioning effects include: 1) the effective desorption of portions of undesirable adsorbed pellicle proteins, in particular those associated with tooth stain binding, calculus development and attraction of undesirable microbial species; 2) creating a hydrophilic tooth surface immediately after treatment; and 3) maintaining surface conditioning effects and control of pellicle film for extended periods following product use, including post brushing and throughout more extended periods. The effect of creating an increased hydrophilic surface can be measured in terms of a relative decrease in water contact angles. The hydrophilic surface, importantly, is maintained on the tooth surface for an extended period after using the product, e.g., tooth brushing.

The polymeric surface active agents that may produce optimal surface conditioning include polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly (acrylate), poly(acrylamide), poly(methacrylate), poly (ethacrylate), poly(hydroxyalkylmethacrylate), poly(vinyl alcohol), poly(maleic anhydride), poly(maleate) poly (amide), poly(ethylene amine), poly(ethylene glycol), poly (propylene glycol), poly(vinyl acetate) and poly(vinyl benzyl chloride); carboxy-substituted polymers; and mixtures thereof. Suitable polymeric surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al. A preferred polymer is diphosphonate modified polyacrylic acid. Polymers with activity must have sufficient surface binding propensity to desorb pellicle proteins and remain affixed to intraoral surfaces. For tooth surfaces, polymers with end or side chain phosphate or phosphonate functions may both be preferred although other polymers with mineral binding activity may prove effective depending upon adsorption affinity.

Suitable phosphonate-containing polymers such as shown below are described in U.S. Pat. No. 5,980,776 to Zakikhani, et al., incorporated herein in its entirety.

1. Co-polymer of Acrylic Acid and Diphosphonic Acid with Structure:

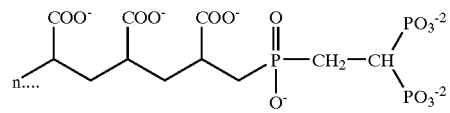

2. Co-polymer of Acrylic Acid and Vinylphosphonic Acid with Structure:

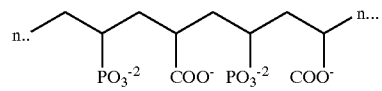

3. Co-polymer of Methacrylic Acid and Vinlyphosphonic Acid with Structure:

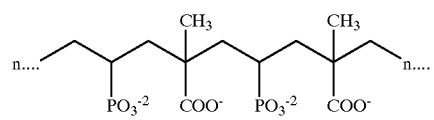

4. Co-polymer of Acrylic acid and Vinlydiphosphonic Acid with Structure:

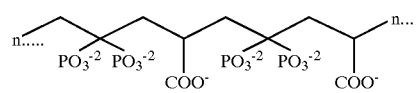

A preferred polymeric surface active agent will be stable with ionic fluoride and will not hydrolyze in high water content formulations, thus permitting a simple single phase dentifrice or mouthrinse formulation. If the polymeric surface active agent does not have these stability properties, it is likely that a dual phase formulation with the polymeric surface active agent separated from the fluoride source will be required.

A preferred polymeric surface active agent is a polyphosphate. A polyphosphate is generally understood to consist of two or more phosphate molecules arranged primarily in a linear configuration, although some cyclic derivatives may be present. Although pyrophosphates and tripolyphosphate are technically polyphosphates, the polyphosphates desired are those having around four or more phosphate molecules so that surface adsorption at effective concentrations produces sufficient non-bound phosphate functions, which enhance the anionic surface charge as well as hydrophilic character of the surfaces. The pyrophosphates are discussed separately under additional anticalculus agents. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). The most preferred polyphosphate is Glass H. These polyphosphates may be used alone or in a combination thereof.

It is also known that polyphosphates with an average chain length greater than about 4 will react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces. It is also known that to have stable polyphosphate, the total water content of the dentifrice composition must be controlled to reduce the hydrolysis of the polyphosphate. U.S. Pat. No. 5,939,052 issued to White, Jr. et al., incorporated herein by reference in its entirety, further describes the polyphosphates. The phosphate sources are also described in more detail in Kirk-Othmer *Encyclopedia of Chemical Technology*, Fourth Edition, Volume 18, Wiley-Interscience Publishers (1996), incorporated herein by reference in its entirety, including all references incorporated into Kirk-Othmer.

The amount of polymeric surface agent required is an effective amount to provide the surface conditioning effects. An effective amount of a polymeric surface active agent will typically be from about 1% to about 35%, preferably from about 2% to about 30%, more preferably from about 5% to about 25%, and most preferably from about 6% to about 20%, by weight of the total oral composition.

In addition to creating the surface conditioning effects, the polymeric surface active agent has been found to solubilize insoluble salts. For example, Glass H has been found to solubilize insoluble stannous salts. The combination of polymeric surface active agent with stannous fluoride provides the desired tartar control, stain control, and surface conditioning, without having a negative effect on the efficacy of the stannous fluoride for the control of dental caries, oral malodor and periodontal diseases including gingivitis.

The surface conditioning effects provided by the present polymeric surface active agents can measured using several different methods. The surface conditioning effects on a subject's teeth and oral mucosa can be quantitatively measured in vivo using both consumer feedback and physical measurement techniques. Quantitative physical in vivo measurements include the water contact angle on the tooth surface and on the mucosal surfaces. The physical chemical surface conditioning effects can also be measured in considerable detail through in vitro methods. In vitro methods are made over time to measure surface free energies and pellicle film thickness and composition.

In vivo studies include a time dependent study to measure the effects of the present composition compared to other dentifrices on aqueous contact angles and consumer subjective responses. In one protocol, panelists are asked to fill out a subjective mouth feel assessment questionnaire including questions on tooth clean feeling, smooth teeth feeling and clean mouth feeling as well as assessments of mouth moisture, following usage of test products. For these tests, subjects reported in the morning to a clinic prior to any oral hygiene or food or beverage consumption. Panelists then had water contact angles taken on air dried tooth and gingival surfaces according to methods disclosed by Baeir et al. ("Biophysical Modeling of Acquired Pellicle Formation on Substrata of Varying Surface Energies," 57th *Colloid and Surface Symposium*, 1983, Abstract No. 49) and Busscher et al. ("Surface Free Energy Changes of Human Enamel During Pellicle Formation. An in vivo Study," Caries Research, 1984, 18: 408–415). Panelists then brushed for one minute with their assigned oral product. After brushing, before lunch and before dinner (late afternoon) subjects again filled out subjective mouth feel questionnaire and had surface contact angles taken. Surface measurements were made in triplicate at each visit on two separate teeth and gingival surfaces.

Results of these tests show that subject's perception of smooth and clean teeth is very poor in the early morning (before brushing) and is improved greatly after brushing with dentifrice compositions. Unfortunately for conventional dentifrice compositions, post brushing maintenance of smooth teeth/clean mouth condition is poor, with perception below neutral by afternoon. Most commercial dentifrice compositions follow this pattern which is disappointing to consumers who expect cleaning effects to last following use.

Use of dentifrice compositions containing polymeric surface active agents (e.g., condensed polyphosphate) according to the present invention produced improved perception scores—which are most noticeable at extended periods following brushing. The condensed phosphate toothpaste resembled Example 1 formulation described in the Examples; the control dentifrice was a commercial sodium fluoride (NaF) dentifrice with silica abrasive (Crest Dentifrice regular flavor, The Procter and Gamble Company, Cincinnati Ohio). Subjects who brushed with polyphosphate dentifrice reported above neutral perception scores up to pre-dinner time period. These improved perception evaluations were compared with measures of surface water contact angles using techniques established by Busscher et al. in the published literature.

Mouth feel perception of clean and smooth teeth followed a pattern identical to that established by contact angle measurements, with lower water contact angle surfaces, that is, more hydrophilic surfaces, apparently correlated with improved consumer perception of clean feeling dentition.

Long term panel studies confirmed that these differences are maintained for extended periods. In product evaluations, the polyphosphate dentifrices which produce hydrophilic conditioning establish far superior overall product satisfaction ratings with consumers.

Laboratory observations permitted more detailed study of physical chemical mechanisms responsible for the product differences. In vitro studies included a time dependent study of dentifrice effects on surface free energies and pellicle film thickness. Bovine enamel blocks were cleaned and polished to standard surfaces. For film thickness measures, dialyzed human saliva was used to produce 16 hour pellicles on tooth surfaces. A subgroup of nontreated specimens was set aside as controls. Further samples were progressed through a series where dentifrice treatments were performed as 30 second immersions in 1:3 part slurries. Following treatment, specimens were re-immersed into standardized dialyzed reconstituted saliva (DRS) media—at 1, 3 and 6 hours post treatment. Subgroups of specimens at each of these times were separated for film thickness measures. Effects of treatments on pellicle film thickness were estimated from X-ray photoelectron spectroscopy (XPS) measurements.

Results show that water treatment produces no changes in film thickness. Conventional dentifrices containing sodium fluoride produce modest film thickness changes which redevelop within 6 hours near pre-treatment levels. Treatment with polyphosphate dentifrice produced a 67% decrease in film thickness post treatment, which was maintained to a greater degree than conventional dentifrice, i.e., up to 6 hours post treatment.

A similar type of model was used to evaluate dentifrice formulation effects on in vitro water contact angles. Pooled whole human saliva modified with dietary extract (to produce in vivo like surface thermodynamic properties) was formed on bovine enamel blocks. Initial water contact angles were measured and paste treatments followed the regimen described for surface film thickness studies. Water contact angles decreased significantly after treatment with the present dentifrice formulations (containing polyphosphate or polyphosphonate) compared to pre-treatment levels. This decreased water contact angle values were shown to be maintained for an extended period of time, up to six hours after treatment.

The effect of surface adsorption of polymeric agents such as polyphosphate on surfaces were further characterized through assessment of effects on surface zeta potential (charge) at apatite surfaces. Powdered enamel (25 um average size) were exposed to dialyzed reconstituted saliva (DRS) to form initial pellicle coverage for periods of 16 hours. Pellicle coated enamel was treated with 25% w/w water slurries of dentifrices for periods of 1 minute, after which specimens were washed with water and resuspended in solutions of variable ionic strength for surface charge determinations. Surface charge was measured by laser electrophoresis tracking of particle mobilities with a Lazer Zee Meter (PenKeim, Bedford Hills, N.Y., USA). Comparisons included water treated control, conventional NaF dentifrice, and dentifrice containing polyphosphate polymer. Measured mobilities were used with equations developed by Ohshima and Kondo (Biophysical Chemistry, 1991, 39: 191–198) to calculate both fixed charge density and electrophoretic softness of enamel surfaces following treatments. The electrophoretic softness is representative of the ion penetratable layer on particle surfaces that depends upon the frictional force exerted on water as it flows through the layer. As softness increases water flows through this layer more freely with less friction. It is believed that this characteristic is associated with mouth feel and chemical effects displayed on intraoral surfaces with selected polymeric agents. Results of testing illustrated that polyphosphate dentifrice produced large changes in fixed charge density (charge was more labile at surface) while the electrophoretic softness decreased dramatically.

The surface conditioning effects of dentifrices may produce numerous intraoral effects including those with both aesthetic and therapeutic advantage. As stated, most of the polyelectrolytes and in particular polyphosphate, polyacrylate and certainly co-polymers of phosphonates and acrylates display significant efficacy toward prevention of dental calculus. The effects of these ingredients on dispersions of dental bacterial adsorption films onto salivary coated conditioning film enamel in a controlled experimental setting were examined. Ultra-thin bovine enamel slabs were coated for 1.5 hours with human whole saliva. Following buffer rinsing, a bacterial suspension of Streptococcus oralis was perfused through the flow chamber at a shear rate of 30 s$^{-1}$ for 4 hours and the number of adhering bacteria $n_{ah}$ was enumerated by image analysis after buffer rinsing at the same shear rate. Then, a 25 weight % dentifrice supernate of conventional NaF dentifrice or polyphosphate/NaF dentifrice was perfused through the flow chamber for 4 min followed by 8 min buffer rinsing and another enumeration of the number of bacteria that had remained adhering $n_{ad}$. Finally, an air-bubble was passed through the flow chamber to mimic the occasionally high detachment forces occurring in the oral cavity and the adhering bacteria nab were counted again. Results illustrate that the polyphosphate dentifrice produced large increases in the desorption of the bacterial strain tested as compared to a conventional dentifrice which did not contain the polyphosphate agent.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. These carriers may be included at levels which do not interfere or prohibit the surface conditioning. The amount of polymeric surface active agent may be increased to account for the additional carriers. Aqueous carriers typically comprise from about 50% to about 99%, preferably from about 70% to about 98%, and more preferably from about 80% to about 95%, by weight of the oral composition.

Fluoride Ion Source

The oral composition of the present invention may incorporate a soluble fluoride source capable of providing free fluoride ions. The fluoride ion source may preferably be in a separate phase than the polymeric surface active agent to aid in stability. Preferred soluble fluoride ion sources include sodium fluoride, stannous fluoride, indium fluoride, and sodium monofluorophosphate. Sodium fluoride and stannous fluoride the most preferred soluble fluoride ion source. Stannous fluoride and methods of stabilization are described in U.S. Pat. No. 5,004,597 issued to Majeti et al. and in U.S. Pat. No. 5,578,293 issued to Prencipe et al., in addition to other sources Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. All patents are incorporated herein by reference in their entirety.

The present compositions contain a soluble fluoride ion source capable of providing from about 50 ppm to about 3500 ppm, and preferably from about 500 ppm to about 3000 ppm of free fluoride ions.

Buffering Agent

The present compositions may contain a buffering agent. Buffering agents, as used herein, refer to agents that can be used to adjust the pH of the compositions to a range of about pH 3 to about pH 10. The oral composition containing a polymeric surface active agent will typically have a slurry pH of from about 4 to about 10, preferably from about 4.5 to about 8, and more preferably from about 5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Stannous Ion Source

The present invention may include a stannous ion source. The stannous ions are provided from stannous fluoride and/or other stannous salt that are added to the oral composition. Stannous fluoride has been found to help in the reduction of gingivitis, plaque, sensitivity, and in improved breath benefits. The stannous provided in an oral composition will provide efficacy to a subject using the composition. Although efficacy could include benefits other than the reduction in gingivitis, efficacy is defined as a noticeable amount of reduction in in situ plaque metabolism as measured by the in vitro Plaque Glycolysis and Regrowth Model (i-PGRM).

The i-PGRM has been demonstrated to provide adequate correlation to bioavailability of stannous fluoride reactivity to be utilized as a predictive measure of antimicrobial, antigingivitis and antiplaque activity of oral compositions containing stannous fluoride. The efficacy of stannous containing compositions for gingivitis can be directly compared to a stannous-containing dentifrice formulation such as described in U.S. Pat. No. 5,004,597 to Majeti et al. and shown as Comparative Example in Example VIII below or to a currently marketed dentifrice containing stannous fluoride, Crest Gum Care.

Stannous fluoride and/or other stannous salts are found in the oral compositions in an effective amount to provide a desired PGRM score. The PGRM score is measured relative to negative control formulations (e.g., non stannous containing compositions) and to positive control formulations containing stannous (e.g., shown in Example VIII below as a Comparative Example). Desired PGRM scores are significantly different from placebo controls and ideally similar to those provided by conventional stannous fluoride compositions proven effective for reducing plaque and gingivitis. Research has demonstrated that significantly effective gingivitis efficacy can be anticipated for compositions providing at least about 60%, preferably at least about 70%, and more preferably at least about 80% of positive control efficacy. It should be realized that differences in antimicrobial potency can be compensated for if not surpassed by improvements in formulation aesthetics for these specially chelated systems; thus, the PGRM scoring relative to the positive control must be considered in this context.

The staining of the tooth surface typically caused by stannous is measured in the clinical situation by using a stain index such as the Lobene or Meckel indices described in the literature. The present inventors have also developed an in vitro staining model which provides quantitative estimates for stannous fluoride formulation staining potential, which correlate well with clinical observations. Formulations can thus be tested in advance of clinical examination using these methods. The present inventors have found that the stain which is typically produced by effective stannous fluoride is reduced by combining the stannous fluoride with one or a mixture of the polymeric surface active agents discussed above. The benefit of reducing the staining caused by stannous is achieved with the present compositions without significantly compromising the efficacy of the stannous, fluoride, and polymeric surface agent. The amount of stain resulting from the oral compositions of the present invention is significantly lower than the amount of staining found in typical dentifrices containing stannous. The term "reduced" as used herein means a statistically significant reduction. Therefore, reducing the staining of stannous means that the amount of stain is statistically significantly reduced relative to a stannous-containing positive control. Not reducing the efficacy of the stannous means the efficacy of the stannous is not statistically significantly reduced relative to a stannous-containing positive control. Alternatively, stain may be measured in relation to typical oral compositions which do not contain stannous fluoride or another antimicrobial agent which is known to stain. Therefore, the compositions may be measured relative to very little to no stain.

Formulations providing efficacy typically include stannous levels provided by stannous fluoride and/or other stannous salts ranging from about 3,000 ppm to about 15,000 ppm stannous ions in the total composition. Below 3,000 ppm stannous the efficacy of the stannous is not sufficient. Preferably, the stannous ion is present in an amount of about 4,000 ppm to about 12,000 ppm, more preferably 5,000 ppm to about 10,000 ppm.

Dentifrices containing stannous salts, particularly stannous fluoride and stannous chloride, are described in U.S. Pat. No. 5,004,597 to Majeti et al., incorporated herein in its entirety. Other descriptions of stannous salts are found in U.S. Pat. No. 5,578,293 issued to Prencipe et al. and in U.S. Pat. No. 5,281,410 issued to Lukacovic et al., incorporated herein in their entirety. In addition to the stannous ion source, other ingredients needed to stabilize the stannous may also be included, such as the ingredients described in Majeti et al. and Prencipe et al.

Other stannous salts include stannous acetate, stannous gluconate, stannous oxalate, stannous sulfate, stannous lactate, and stannous tartrate. The preferred stannous ion sources are stannous fluoride and stannous chloride dihydrate. The combined stannous salts may be present in an amount of from about 0.1% to about 11%, by weight of the total composition. Preferably, the stannous salts may be present in an amount of from about 0.5 to about 7%, more preferably from about 1% to about 5%, and most preferably from about 1.5% to about 3% by weight of the total composition.

Anticalculus Agent

Optional agents that may be used in combination with the polymeric surface active agent include such materials known to be effective in reducing calcium phosphate mineral deposition related to calculus formation. Pyrophosphate salts may be used in the present invention as anticalculus agents or as buffering agents, as long of the surface conditioning effects of the polymeric surface active agent is not eliminated. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate may be undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk-Othmer *Encyclopedia of Chemical Technology*, Third Edition, Volume 17, Wiley-Interscience Publishers (1982), incorporated herein by reference in its entirety, including all references incorporated into Kirk-Othmer.

Additional anticalculus agents include other materials known to be effective in reducing calcium phosphate mineral deposition related to calculus formation. Agents included are synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

An abrasive polishing material may also be included in the oral compositions. The abrasive polishing material contemplated for use in the compositions of the present invention can be any material which does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Silica abrasives are also described in Rice, U.S. Pat. Nos. 5,589,160; 5,603,920; 5,651,958; 5,658,553; and 5,716,601; herein incorporated by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the oral composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The present invention provides compositions in the form of toothpastes, dentifrices, tooth powder, topical oral gels, mouthrinses, denture product, mouthsprays, lozenges, oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water employed in the preparation of commercially suitable oral compositions should preferably be of low ion content and free of organic impurities. Water will generally comprise from about 5% to about 70%, and preferably from about 10% to about 50%, by weight of the composition herein. The polymeric surface active agent may require a lower level of water to be stable. Generally, the level of water is up to about 20%, preferably from about 5% to about 14%, and more preferably from about 7% to about 12%, by weight of the oral composition. The amounts of water include the free water which is added plus that which is introduced with other materials, such as with sorbitol, silica, surfactant solutions, and/or color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey, incorporated herein by reference. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. The water insoluble antimicrobial agents, water soluble agents, and enzymes may be present in either the first or second dentifrice compsoitions. The quaternary ammonium agents, stannous salts, and substituted guanidines are preferably present in an oral composition separate from the polymeric surface active agent. These agents may be present at levels of from about 0.01% to about 1.5%, by weight of the dentifrice composition.

The oral compositions of the present invention are in the form of toothpastes, dentifrices, topical oral gels, mouthrinses, denture products, mouthsprays, lozenges, oral tablets, or chewing gums. The dentifrice compositions may be a paste, gel, or any configuration or combination thereof. If a dual phase formulation is used, it is preferred that the dentifrice compositions be physically separated. Also for aesthetics reasons, it is preferred that one composition be a paste and the other composition be a gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

Method of Treatment

The present invention also relates to methods for reducing the incidence of calculus on dental enamel and to methods for providing surface conditioning effects. The present invention also relates to methods of providing clean mouth and tooth feel, smooth teeth feel, and longer lasting clean or smooth tooth feel. The benefits of these compositions may increase over time when the composition is repeatedly used.

The method of treatment herein comprises contacting a subject's dental enamel surfaces and mucosa in the mouth with the oral compositions according to the present invention. The method of treatment may be by brushing with a dentifrice or rinsing with a dentifrice slurry or mouthrinse. Other methods include contacting the topical oral gel, dentures product, mouthspray, or other form with the subject's teeth and oral mucosa. The subject may be any person or lower animal whose tooth surface contact the oral composition.

It should be understood that the present invention relates not only to methods for delivering the present polymeric surface active agent containing compositions to the oral cavity of a human, but also to methods of delivering these compositions to the oral cavity of other animals, e.g., household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the polymeric surface active agent is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES & METHOD OF MANUFACTURING

The following examples further describe and demonstrate embodiments within the scope of the present invention. These examples are given solely for the purpose of illustration and are not to be construed as limitations of the present invention as many variations thereof are possible without departing from the spirit and scope.

| EXAMPLE I | | | |
|---|---|---|---|
| First Dentifrice Composition | | Second Dentifrice Composition | |
| Ingredient | Wt. % | Ingredient | Wt. % |
| Carboxymethycellulose | 0.60 | Color | 0.30 |
| Water | 7.00 | Water | 33.0 |
| Flavor | 1.00 | Flavor | 0.40 |

-continued

| Ingredient | Wt.% | Ingredient | Wt.% |
|---|---|---|---|
| Glycerin | 43.2 | Glycerin | 44.514 |
| Poloxamer 407 | 5.00 | Poloxamer 407 | 21.00 |
| Propylene Glycol | 5.00 | Sodium Fluoride | 0.486 |
| Sodium Alkyl Sulfate[a] | 4.00 | Sodium Saccharin | 0.30 |
| Silica | 20.0 | | |
| Sodium Carbonate | 2.00 | | |
| Sodium Saccharin | 0.50 | | |
| Titanium Dioxide | 0.50 | | |
| Xanthan Gum | 0.20 | | |
| Glass H Polyphosphate | 7.00 | | |
| Polyethylene Glycol | 3.00 | | |
| Calcium Peroxide | 1.00 | | |

EXAMPLE II

| Ingredient | Wt.% | Ingredient | Wt.% |
|---|---|---|---|
| Carboxymethycellulose | 0.60 | Carbomer | 0.200 |
| Water | 7.00 | Color | 0.400 |
| Flavor | 1.00 | Water | 25.1 |
| Glycerin | 26.8 | Flavor | 0.90 |
| Poloxamer 407 | 5.00 | Glycerin | 9.00 |
| Propylene Glycol | 5.00 | Polyethylene Glycol | 3.00 |
| Sodium Alkyl Sulfate[a] | 4.00 | Sodium Alkyl Sulfate[a] | 4.00 |
| Silica | 22.0 | Silica | 22.5 |
| Sodium Bicarbonate | 15.0 | Sodium Saccharin | 0.50 |
| Sodium Carbonate | 2.00 | Sorbitol | 29.594 |
| Sodium Saccharin | 0.50 | Sodium Acid Pyrophosphate | 0.50 |
| Titanium Dioxide | 0.50 | | |
| Xanthan Gum | 0.20 | Tetrasodium Pyrophosphate | 3.22 |
| Glass H Polyphosphate | 7.00 | | |
| Polyethylene Glycol | 3.00 | Xanthan Gum | 0.60 |
| Calcium Peroxide | 0.40 | Sodium Fluoride | 0.486 |

EXAMPLE III

| Ingredient | Wt.% | Ingredient | Wt.% |
|---|---|---|---|
| Carboxymethycellulose | 0.60 | Carbomer | 0.200 |
| Water | 7.00 | Color | 0.400 |
| Flavor | 1.00 | Water | 25.1 |
| Glycerin | 24.2 | Flavor | 0.90 |
| Poloxamer 407 | 5.00 | Glycerin | 9.00 |
| Propylene Glycol | 5.00 | Polyethylene Glycol | 3.00 |
| Sodium Alkyl Sulfate[a] | 4.00 | Sodium Alkyl Sulfate[a] | 4.00 |
| Silica | 22.0 | Silica | 22.5 |
| Sodium Bicarbonate | 15.0 | Sodium Saccharin | 0.50 |
| Sodium Carbonate | 2.00 | Sorbitol | 29.644 |
| Sodium Saccharin | 0.50 | Sodium Acid Pyrophosphate | 0.75 |
| Titanium Dioxide | 0.50 | | |
| Xanthan Gum | 0.20 | Tetrasodium Pyrophosphate | 2.92 |
| Sodaphos Polyphosphate | 7.00 | | |
| Polyethylene Glycol | 3.00 | Xanthan Gum | 0.60 |
| Calcium Peroxide | 3.00 | Sodium Fluoride | 0.486 |

EXAMPLE IV

| Ingredient | Wt.% | Ingredient | Wt.% |
|---|---|---|---|
| Carboxymethycellulose | 0.60 | Carbomer | 0.200 |
| Water | 7.00 | Color | 0.400 |
| Flavor | 1.00 | Water | 22.834 |
| Glycerin | 27.2 | Flavor | 0.90 |
| Poloxamer 407 | 5.00 | Glycerin | 9.00 |
| Propylene Glycol | 5.00 | Polyethylene Glycol | 3.00 |
| Sodium Alkyl Sulfate[a] | 4.00 | Sodium Alkyl Sulfate[a] | 4.00 |
| Silica | 22.0 | Silica | 22.5 |
| Sodium Bicarbonate | 15.0 | Sodium Saccharin | 0.50 |
| Sodium Carbonate | 2.00 | Sorbitol | 24.00 |
| Sodium Saccharin | 0.50 | Sodium Acid Pyrophosphate | 2.10 |
| Titanium Dioxide | 0.50 | | |
| Xanthan Gum | 0.20 | Tetrasodium Pyrophosphate | 2.05 |
| Glass H Polyphosphate | 7.00 | | |
| Polyethylene Glycol | 3.00 | Xanthan Gum | 0.60 |
| | | Sodium Fluoride | 0.486 |
| | | Triclosan | 0.60 |
| | | Tetrapotassium Pyrophosphate[b] | 6.830 |

EXAMPLE V

| Ingredient | Wt.% | Ingredient | Wt.% |
|---|---|---|---|
| Carboxymethycellulose | 0.60 | Carbomer | 0.200 |
| Water | 7.00 | Color | 0.400 |
| Flavor | 1.00 | Water | 25.1 |
| Glycerin | 31.2 | Flavor | 0.90 |
| Poloxamer 407 | 5.00 | Glycerin | 9.00 |
| Propylene Glycol | 5.00 | Polyethylene Glycol | 3.00 |
| Sodium Alkyl Sulfate[a] | 4.00 | Sodium Alkyl Sulfate[a] | 4.00 |
| Silica | 27.0 | Silica | 22.5 |
| Sodium Bicarbonate | 5.0 | Sodium Saccharin | 0.50 |
| Sodium Carbonate | 2.00 | Sorbitol | 33.314 |
| Sodium Saccharin | 0.50 | Xanthan Gum | 0.60 |
| Titanium Dioxide | 0.50 | Sodium Fluoride | 0.486 |
| Xanthan Gum | 0.20 | | |
| Glass H Polyphosphate | 7.00 | | |
| Polyethylene Glycol | 3.00 | | |
| Calcium Peroxide | 1.00 | | |

EXAMPLE VI

| First Dentifrice Composition | | Second Dentifrice Composition | |
|---|---|---|---|
| Ingredient | Wt.% | Ingredient | Wt.% |
| CMC 7M8SF | 0.100% | Carbomer 956 | 1.000% |
| USP Water | 2.300% | Cocamidopropyl Betaine[b] | 2.900% |
| Flavor | 1.600% | Color-FD&C Blue #1 Sol'n | 0.300% |
| Glass H, sieved to <210 m | 14.000% | USP Water | 10.000% |
| Glycerin | 42.300% | Flavor | 1.600% |
| PEG-12/PEG 600 | 1.000% | Glycerin | 30.087% |
| Poloxamer 407 | 0.500% | SLS[a] | 2.000% |
| Polyethylene Oxide | 0.500% | Silica-Zeodent 119 | 20.000% |
| Propylene Glycol | 4.600% | Sodium Fluoride | 0.512% |
| SLS[a] | 4.000% | Sodium Hydroxide | 0.800% |
| Silica-Zeodent 119 | 20.000% | Sodium Saccharin | 0.400% |
| Silica Thickening | 1.000% | Sorbitol | 30.301% |
| Sodium Bicarbonate | 5.000% | Xanthan Gum | 0.100% |
| Sodium Hydroxide | 1.800% | | |
| Sodium Saccharin | 0.400% | | |
| Titanium Dioxide-Rutile | 0.500% | | |
| Xanthan Gum | 0.400% | | |

EXAMPLE VII

First Dentifrice Composition

| Ingredient | Formula A | Formula B | Formula C | Formula D |
|---|---|---|---|---|
| Carboxymethycellulose | 0.500 | 0.200 | 0.400 | 0.300 |
| Water | 2.768 | — | — | 1.400 |
| Flavor | 1.000 | 1.300 | 1.200 | 1.100 |
| Glycerin | 36.432 | 45.000 | 42.650 | 39.850 |
| Polyethylene Glycol | 8.000 | — | 4.000 | 6.000 |
| Propylene Glycol | 8.000 | — | — | — |
| Sodium Lauryl Sulfate[a] | 4.000 | 8.000 | 10.000 | 6.000 |
| Silica | 22.000 | 18.500 | 20.000 | 26.000 |
| Benzoic Acid | 0.600 | — | — | 0.300 |
| Sodium Benzoate | 0.600 | — | — | 0.300 |
| Sodium Saccharin | 0.300 | 0.400 | 0.450 | 0.350 |
| Titanium Dioxide | 0.500 | 0.500 | 0.300 | 0.400 |
| Glass H Polyphosphate | 15.000 | 26.000 | 21.000 | 18.000 |
| Xanthan Gum | 0.300 | 0.100 | — | — |
| Total | 100.000 | 100.000 | 100.000 | 100.000 |

Second Dentifrice Composition

| Ingredient | Formula 1 | Formula 2 | Formula 3 | Formula 4 |
|---|---|---|---|---|
| Polyoxyethylene | — | 0.200 | — | — |
| Water | 21.840 | 49.158 | 33.258 | 12.000 |
| Flavor | 1.500 | 1.300 | 1.200 | 1.100 |
| FD&C Blue #1 Dye Sol'n | 0.300 | 0.300 | 0.100 | 0.500 |
| Glycerin | 30.466 | 22.000 | 42.650 | — |
| Polyethylene Glycol | — | — | — | 6.000 |
| Poloxamer 407 | 15.500 | 17.500 | 17.500 | 7.000 |
| Sodium Lauryl Sulfate[a] | 4.000 | 2.500 | — | 7.500 |
| Silica | 23.000 | — | — | 20.000 |
| Sodium Gluconate | 3.290 | 2.760 | 2.390 | 4.135 |

-continued

| | | | | |
|---|---|---|---|---|
| Stannous Fluoride | 0.908 | 1.062 | 1.062 | — |
| Stannous Chloride | 0.300 | 1.320 | 0.940 | — |
| Stannous Sulfate | | | | 2.851 |
| Sodium Hydroxide[b] | 0.746 | 0.700 | 0.600 | 0.900 |
| Sodium Saccharin | 0.400 | 0.400 | 0.300 | 0.400 |
| Sodium Fluoride | — | — | — | 0.486 |
| Sorbitol[c] | — | — | — | 35.528 |
| Xanthan Gum | — | 0.800 | — | 1.100 |
| Hydroxyethyl Cellulose | — | — | — | 0.500 |
| Total | 100.000 | 100.000 | 100.000 | 100.000 |

[a]27.9% solution
[b]60% solution
[a]27.9% solution
[b]30% solution
[a]27.9% solution
[a]27.9% solution
[b]50% solution
[c]70% solution The first dentifrice compositions of the dual-phase compositions are prepared as follows. Add the water and/or sodium lauryl sulfate solution and water soluble salts to main mixing vessel. In a separate vessel, disperse thickeners in glycerin. Add this glycerin slurry to the mixing vessel, mixing well. Add the propylene glycol and polyethylene glycol to the mixing vessel and mix until well dispersed. Next add titanium dioxide and silica. Mix well. Cool the mixing vessel to less than 30° C. and add the polyphosphate. Mix until homogeneous.

The second dentifrice compositions are prepared as follows. Add glycerin and/or sorbitol/polyethylene glycol to the main mix tank. Add thickeners, non-ionic surfactants, flavors, stannous salts, fluoride, and other soluble salts to the main mix vessel. Mix/homogenize until well dispersed and homogeneous. Add water to the main mix tank and mix/homogenize until the salts and surfactants have dissolved, the thickeners are hydrated and the mix is homogeneous. Add sodium hydroxide and color and mix well. Add sodium lauryl sulfate solution and mix until homogeneous. Cool batch to less than 30° C.

EXAMPLE VIII

| Ingredient | Formula A | Formula B | Formula C | Formula D | Comparative Example |
|---|---|---|---|---|---|
| Flavor | 1.000 | 1.200 | 1.500 | 1.150 | 1.000 |
| Glycerin | 53.166 | 54.300 | 52.872 | 9.000 | 14.425 |
| Poloxamer 407 | 5.000 | 3.000 | 8.000 | — | — |
| Stannous Chloride | 0.680 | — | — | — | 1.500 |
| Stannous Sulfate | — | 1.460 | — | — | — |
| Stannous Fluoride | 0.454 | — | — | — | 0.454 |
| Sodium Fluoride | — | 0.320 | — | 0.243 | — |
| Sodium Monofluorophosphate | — | — | 1.128 | — | — |
| Sodium Lauryl Sulfate[a] | 7.500 | 6.000 | 4.000 | 4.000 | 5.000 |
| Silica | 20.000 | 18.000 | 22.000 | 22.000 | 20.000 |
| Carboxymethyl Cellulose | 0.200 | 0.200 | 0.400 | — | 0.600 |
| Sodium Gluconate | — | 1.470 | — | — | 2.100 |
| Sodium Saccharin | 0.400 | 0.350 | 0.500 | 0.460 | 0.300 |
| Titanium Dioxide | 0.500 | 0.500 | 0.500 | — | 0.525 |
| Xanthan Gum | 0.100 | 0.200 | 0.100 | 0.600 | 0.700 |
| Glass H | 11.000 | 13.000 | 9.000 | — | — |
| Poly (diphosphonate/acrylate) | — | — | — | 5.000 | — |
| Na hydroxide[b] | — | — | — | trace | 0.600 |
| FD&C Blue #1[c] | — | — | — | — | 0.300 |
| Sorbitol[d] | | | | 28.937 | 37.496 |
| Carbopol | | | | 0.200 | — |
| Polyethylene Glycol | | | | 3.000 | — |
| Water | | | | 25.410 | 15.000 |

[a]27.9% solution
[b]50% solution
[c]1% solution
[d]70% solution

Example VIII compositions (Formula A–D) are prepared as follows. Add the glycerin and thickening agents to the main mix tank and mix until homogeneous. If applicable, add the sodium gluconate to the main mix tank and mix until homogeneous. Add the sodium lauryl sulfate solution and flavor to the main mix tank and mix until thickeners are hydrated/dissolved. Add the silica and titanium dioxide to the main mix tank and mix until homogeneous. Add stannous and/or fluoride salts to the main mix tank and mix until homogeneous. Finally add the polymeric surface active agent (Glass H or polyphosphonate) to the main mix tank. Mix until homogeneous.

The comparative example of a stannous-containing dentifrice is prepared as follows as described in U.S. Pat. No. 5,004,597 to Majeti, et al. Sorbitol and one half of the water are added to the mix tank and heating to 77° C. initiated. Saccharin, titanium dioxide, and silica may be added to the mixture during this heating period. Sufficient agitation is maintained to prevent the settling of the insoluble components. The glycerin is added to a separate vessel and is also heated to 77° C. When both the solutions have attained the required temperature, the carboxymethyl cellulose (CMC) is slowly added to the glycerin under vigorous agitation. When the CMC is sufficiently dispersed in the glycerin, this mixture is added to the sorbitol/water mixture. The resulting mixture is then blended for a period of time sufficient to allow complete hydration of the binders (about 15 minutes). When the paste is of acceptable texture, the flavor, sodium alkyl sulfate, and color are added. One half of the remaining water is then added to a separate mix tank and allowed to heat to 77° C. After the water attains the necessary temperature, the sodium gluconate is added under medium agitation and allowed to dissolve completely. The stannous chloride dihydrate is then added to the gluconate solution and also allowed to dissolve. This mixture is added to the main mix. The stannous fluoride is added to the remaining water (also at 77° C.) and the resulting solution is added to the main mix and allowed to blend thoroughly before final pH adjustment with sodium hydroxide. The completed paste is agitated for approximately 20 minutes before being milled and deaerated.

What is claimed is:

1. A method of providing surface conditioning effects to a subject's teeth and mucosal surfaces comprising administering to the subject's oral cavity an oral composition comprising a polymeric surface active agent which is a polyphosphate having about four or more phosphate groups, wherein the oral composition has a total water content of less than about 20% and wherein the surface conditioning effects comprise (a) increased hydrophilic character of the surface as measured by a decrease in water contact angles or an increase in anionic surface charge and surface charge density and (b) decreased pellicle film thickness.

* * * * *